(12) United States Patent
Fenchel et al.

(10) Patent No.: US 11,756,243 B1
(45) Date of Patent: Sep. 12, 2023

(54) COMPUTER-IMPLEMENTED METHOD FOR DETERMINING NUCLEAR MEDICAL IMAGE DATA SETS IN DYNAMIC NUCLEAR MEDICAL IMAGING, DETERMINING DEVICE AND ELECTRONICALLY READABLE STORAGE MEDIUM

(71) Applicant: Siemens Healthcare GmbH, Erlangen (DE)

(72) Inventors: Matthias Fenchel, Erlangen (DE); Thomas Vahle, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 18/173,951

(22) Filed: Feb. 24, 2023

(30) Foreign Application Priority Data

Feb. 28, 2022 (EP) ..................................... 22159187

(51) Int. Cl.
*G06T 11/00* (2006.01)
*G06T 7/00* (2017.01)
*A61B 5/055* (2006.01)

(52) U.S. Cl.
CPC ............ *G06T 11/008* (2013.01); *A61B 5/055* (2013.01); *G06T 7/0012* (2013.01); *G06T 2207/10088* (2013.01); *G06T 2207/10104* (2013.01); *G06T 2207/20084* (2013.01)

(58) Field of Classification Search
CPC .................. G06T 11/008; G06T 7/0012; G06T 2207/10088; G06T 2207/10104; G06T 2207/20084; A61B 5/055

USPC .......................................................... 382/131
See application file for complete search history.

(56) References Cited

U.S. PATENT DOCUMENTS

| | | | |
|---|---|---|---|
| 2018/0197317 A1* | 7/2018 | Cheng ................... | G06T 11/006 |
| 2020/0118307 A1* | 4/2020 | Boada ................... | G06T 11/006 |
| 2021/0366169 A1* | 11/2021 | Liu ....................... | A61B 6/5205 |
| 2022/0287671 A1* | 9/2022 | Huang ................... | G06N 3/045 |
| 2022/0319069 A1* | 10/2022 | Hu ........................ | A61B 6/037 |
| 2022/0383565 A1* | 12/2022 | Zhu ....................... | G06T 11/006 |

FOREIGN PATENT DOCUMENTS

WO    WO-2021259720 A1 * 12/2021
WO    WO 2021259720 A1    12/2021

OTHER PUBLICATIONS

Tong Shan et al.:"Image reconstruction for PET/CT scanners: past achieve-ments and future challenges", Imaging Med. 2(5), 2010, pp. 529-545.

(Continued)

*Primary Examiner* — Van D Huynh
(74) *Attorney, Agent, or Firm* — Harness, Dickey & Pierce, P.L.C.

(57) ABSTRACT

Computer-implemented method for determining nuclear medical image data sets in dynamic nuclear medical imaging. The method includes using a trained function to determine at least one further nuclear medical image data set for at least one frame if a basis raw data set is taken from one single frame, wherein input data of the trained function includes at least one of the nuclear medical raw data set of the respective frame or a preliminary reconstructed image reconstructed therefrom, and an already determined nuclear medical image data set.

20 Claims, 7 Drawing Sheets

(56) References Cited

OTHER PUBLICATIONS

Maes F. et al.:"Medical Image Registration Using Mutual Information", Proceedings of the IEEE, Oct. 2003, pp. 1699-1722, vol. 91 (No. 10), IEEE.

Schramm G. et al.:"Approximating anatomically-guided PET reconstruction in image space using a convolutional neural network", Neu-roimage 2024 (2021), p. 117399.

Rigie et al.:"Approximating MRI-Based Anatomically Guided PET Reconstruction with a Convolutional Neural Network," 2018 IEEE Nuclear Science Symposium and Medical Imaging Conference Proceedings (NSS/MIC), Sydney, Australia, 2018,, pp. 1-3, doi: 10.1109/NSSMIC.2018.8824500.

Bowhser J.E. et al.:"Utilizing MRI Information to Estimate F18-FDG Distribu-tions in Rat Flank Tumors", IEEE 2004.

Sanaat Amirhossein et al: "Fast dynamic brain PET imaging using stochastic variational prediction for recurrent frame generation", Medical Physics., vol. 48, No. 9, Jun. 26, 2021 (Jun. 26, 2021), pp. 5059-5071, XP055949305, US ISSN: 0094-2405, DOI: 10.1002/mp.15063; the whole document; 2021.

Extended European Search Report dated Sep. 6, 2022.

\* cited by examiner

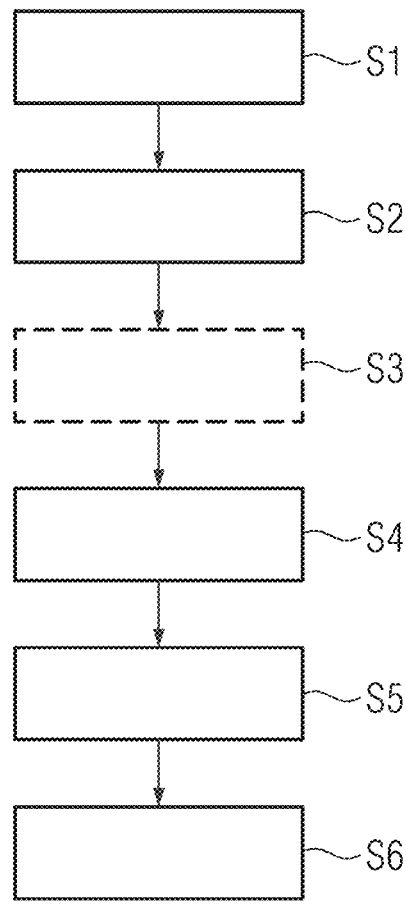
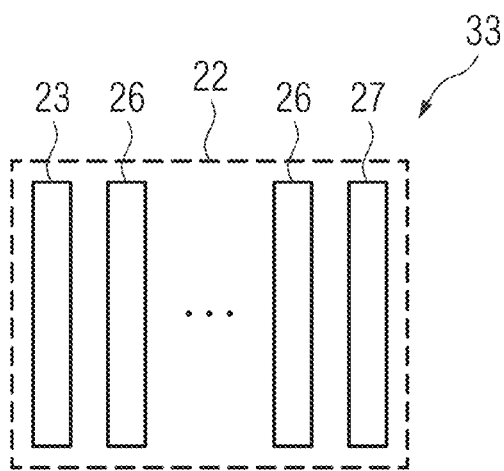

COMPUTER-IMPLEMENTED METHOD FOR DETERMINING NUCLEAR MEDICAL IMAGE DATA SETS IN DYNAMIC NUCLEAR MEDICAL IMAGING, DETERMINING DEVICE AND ELECTRONICALLY READABLE STORAGE MEDIUM

CROSS-REFERENCE TO RELATED APPLICATION(S)

The present application claims priority under 35 U.S.C. § 119 to European Patent Application No. 22159187.8, filed Feb. 28, 2022, the entire contents of which are incorporated herein by reference.

FIELD

One or more example embodiments of the present invention concerns a computer-implemented method for determining nuclear medical image data sets in dynamic nuclear medical imaging, wherein nuclear medical raw data sets of a field of view acquired over a time interval, wherein the time interval comprises a progression period of a tracer in the field of view and each nuclear medical raw data set is acquired in one of multiple time frames, into which the time interval is divided, and an anatomical image showing the anatomy in the field of view are provided. One or more example embodiments of the present invention further concerns a determining device, a computer program and an electronically readable storage medium.

RELATED ART

Nuclear medical imaging (sometimes also called emission tomography), in particular positron emission tomography (PET) and single photon emission computer tomography (SPECT), are imaging techniques in which radioactive substances, so-called tracers, inside the body of a patient are detected. In other words, radiation emitted from within the body is measured by corresponding detectors. From the resulting nuclear medical raw data sets, in particular list-mode data sets, which describe radiation measuring events, nuclear medical image data sets showing the distribution of the tracer may be reconstructed.

Here, back projection methods, for example filtered back projection, may be applied and attenuation corrections based on attenuation maps, which may, for example, be derived from anatomical images of other modalities, may be performed. Such preliminary backprojected images, which are not attenuation corrected, may also be called NAC images, while attenuation-corrected preliminary backprojected images are often called AC images. However, such preliminary backprojected images are often of a low quality, in particular because of noise. In particular, the degrading factors in a nuclear medical imaging device may not be modelled and the stochastic variability in photon detection cannot be taken into account. Hence, advanced reconstruction methods have been proposed.

One of those advanced reconstruction methods comprises iterative image reconstruction. Here, the statistical noise of nuclear medical data and physical effects of the imaging process can be modelled, leading to improved performance. For example, a preliminary backprojected image may be used as a first assumption, which is then optimized by repeatedly forward-projecting and comparing to the original nuclear medical raw data. Correction terms are computed based on the difference of projected and measured data and backprojected to update the preliminary image. Based on the comparison, the estimate is adjusted due to certain criteria. Further approaches include partitioning the nuclear medical raw data into subsets and use only one subset for each update. This approach is also called OSEM—ordered subsets expectation maximization. For more on these classical iterative reconstruction approaches, it is exemplarily referred to Shan Tong et al., "Image reconstruction for PET/CT scanners: past achievements and future challenges", Imaging Med. 2(5), 2010, pages 529-545. In addition, expectation maximization (EM) algorithms have been proposed used to find a maximum likelihood image estimate. This method is usually called MLEM—maximum likelihood expectation maximization.

Since nuclear medical imaging has relatively low resolution compared with anatomical imaging modalities like computer tomography (CT) and magnetic resonance imaging (MRI), the possibility of incorporating anatomical information into nuclear medical image reconstruction was also researched. Approaches which define a prior and use a Bayesian likelihood term to combine with expectation maximation algorithms have been proposed. A well-known exemplary reconstruction technique is an EM reconstruction based on a maximum likelihood term, wherein a so-called Bowsher prior is used, has, for example, been proposed in James E. Bowsher et al. in "Utilizing MRI Information to Estimate F18-FDG Distributions in Rat Flank Tumors", IEEE 2004.

However, while such reconstruction approaches incorporating anatomical information via a prior are already computationally expensive as such, they also require an optimally aligned anatomical image, for example an MRI image, as input. As a consequence, a multi-modal registration has to be performed before every iterative reconstruction, which is also computationally expensive. While, regarding the Bowsher reconstruction as such, it has already been proposed to use artificial intelligence, in particular a convolutional neural network, a registration still has to be performed. In an article by D. Rigie et al., "Approximating AI-based anatomically guided PET reconstruction with a convolutional neural network", 2018 IEEE Nuclear Science Symposium and Medical Imaging Conference Proceedings (NSS/MIC), Sydney, Australia, 2018, pages 1-3, it has been shown that the results of an analytical iterative reconstruction using a Bowsher prior can also be achieved entirely in the image domain with a convolutional neural network (CNN). In particular, anatomically-guided PET reconstruction using the asymmetric Bowsher prior can be well approximated by a purely shift-invariant CNN in image space allowing the generation of anatomically-guided PET images in almost real-time. However, such approaches using trained functions still need optimal registration between the anatomical image and the nuclear medical raw data.

SUMMARY

The mentioned problem is particularly relevant regarding dynamic nuclear medical imaging. Here, the imaging time interval is divided into multiple frames, wherein, for each frame, a nuclear medical image data set is determined to be able to evaluate the propagation of the tracer in the field of view as well as other aspects. Due to the shorter acquisition time per frame, the frame-specific nuclear medical images of dynamic studies are usually lower in quality, since less events are recorded. Registering the anatomical image to the respective nuclear raw data set and, consecutively, performing an analytical iterative reconstruction using a prior or applying a trained function for each frame, results in a very time-consuming process. Hence, the computational effort grows considerably with the number of frames. Due to lower count rates in the frames and larger amounts of motion throughout a dynamic study, registration quality may be impacted and registration results can be suboptimal or even limited to specific tracers with substantial non-focal background uptake.

One or more example embodiments reconstructs high-quality nuclear medical image data sets for each frame in a dynamic nuclear medical imaging study.

According to one or more example embodiments of the present invention, improvements are achieved by providing a computer-implemented method, a determining device, a computer program and an electronically readable storage medium according to the independent claims. Advantageous embodiments are described in the dependent claims.

BRIEF DESCRIPTION OF THE DRAWINGS

Objects and features of one or more example embodiments of the present invention will become apparent from the following detailed description considered in conjunction with the accompanying drawings. The drawings, however, are only principle sketches designed solely for the purpose of illustration and do not limit the invention. The drawings show.

DETAILED DESCRIPTION

Figure 1:
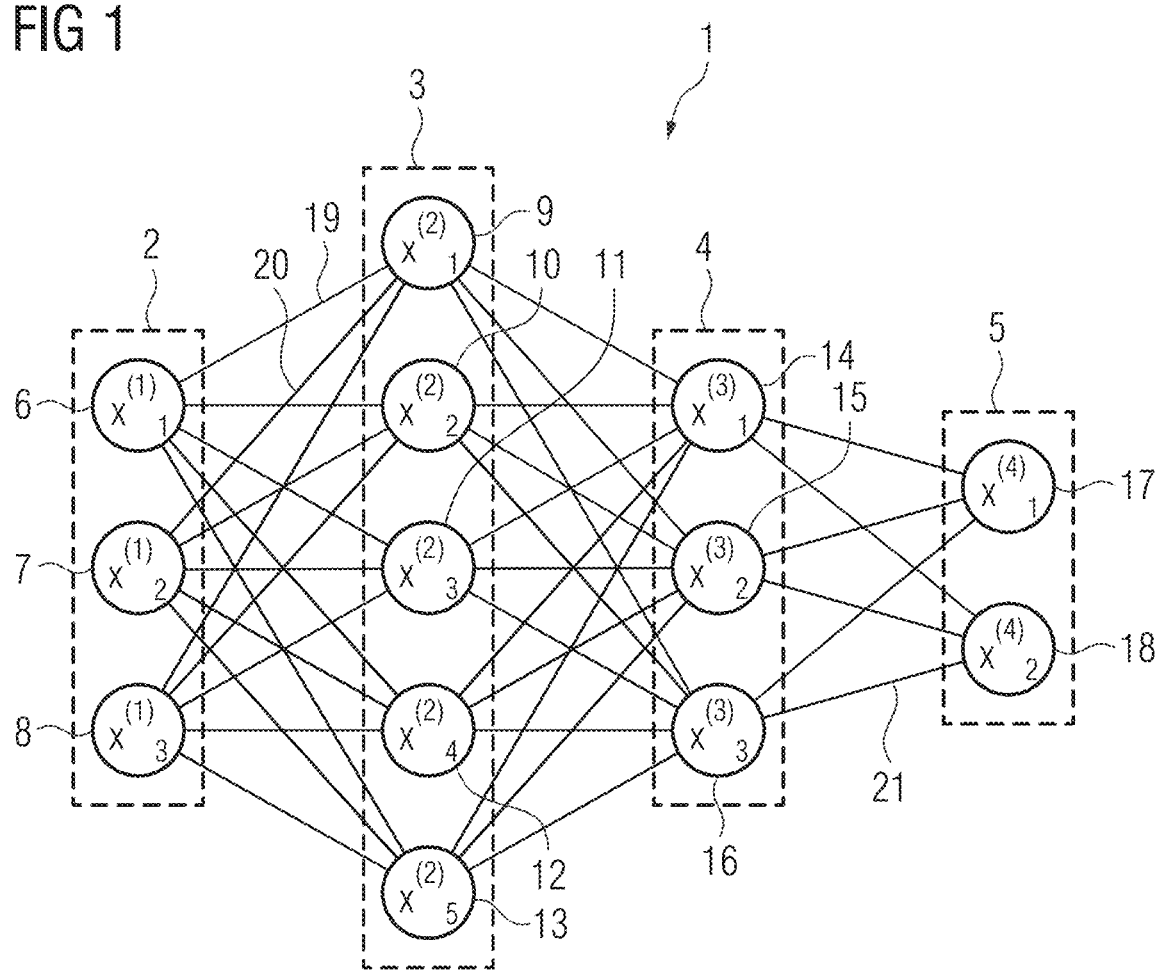
FIG. 1 an embodiment of a neural network,
FIG. 2 an embodiment of a convolutional neural network,
FIG. 3 a general flowchart of embodiments of a method according to the invention,
FIG. 4 an exemplary structure of a second trained function,
FIG. 5 a first embodiment of a method,
FIG. 6 a second embodiment of a method,
FIG. 7 a third embodiment of a method, and
FIG. 8 the functional structure of a determining device according to one or more example embodiments of the invention.

The computer-implemented method for determining nuclear medical image data sets in dynamic nuclear medical imaging according to one or more example embodiments of the present invention comprises:

providing nuclear medical raw data sets of a field of view acquired over a time interval, wherein the time interval comprises a progression period of a tracer in the field of view and each nuclear medical raw data set is acquired in one of multiple time frames, into which the time interval is divided, providing an anatomical image showing the anatomy in the field of view, selecting at least one of the nuclear medical raw data sets as a basis raw data set, reconstructing a first nuclear medical image data set by either iterative reconstruction of the basis raw data set using a prior based on the anatomical image to incorporate anatomical information, or using a first trained function applying such an iterative reconstruction to the anatomical image, and the basis raw data set and/or a preliminary reconstructed data set thereof, using a second trained function to determine at least one further nuclear medical image data set for, if the basis raw data set is taken from one single frame, at least one other frame, in particular all other frames, else, at least one frame, in particular all frames, as output data, wherein input data of the second trained function comprises the nuclear medical raw data set of the respective frame and/or a preliminary reconstructed image reconstructed therefrom, and an already determined nuclear medical image data set.

Here, the already determined nuclear medical image data set may be the first nuclear medical image data set, in particular for the first of the further nuclear medical image data sets. However, it is also possible that the already determined nuclear medical image data set comprises a further nuclear medical image data set, for example an already determined further nuclear medical image data set of a neighboring frame. In particular, the already determined nuclear medical image data set of a frame adjacent in time may be used. For example, starting from one single frame chosen as the basis raw data set, the at least one frame directly adjacent in time may be determined first using the first nuclear medical image data set as input, whereafter the next adjacent frame may be determined using the first further nuclear medical image data set as input, and so on. If, for example, the basis raw data set only comprises the nuclear medical raw data set of the first frame, the first nuclear medical image data set already serves as a result for the first frame, whereafter, using the second trained function, the nuclear medical image data set for the second frame is determined based on the result for the first frame, the nuclear medical image data set for the third frame is determined based on the result for the second frame, and so on until the last frame. However, in other embodiments, it is also possible to always use the first nuclear medical image data set as input data for all frames/all other frames.

In the method according to one or more example embodiments of the present invention, in a first step, a first nuclear medical image data set is determined using a standard analytical iterative reconstruction approach or a first trained function "mimicking" this approach and being trained by its results. Input data for the first trained function hence comprises a) the anatomical image and b) the basis raw data set and/or a preliminary reconstructed, for example backprojected, data set (image) thereof. Here, as will be discussed later on, multi-modality co-registration either is not necessary or has to be performed only once for this first reconstruction, which may be understood as a nuclear medical prior image. For example, for reconstruction, an analytical MLEM nuclear medical reconstruction with a Bowsher prior or a first trained function as suggested in the already cited article by D. Rigie et al. or the similar article by Georg Schramm et al., "Approximating anatomically-guided PET reconstruction in image space using a convolutional neural network", Neuroimage 2024 (2021), page 117399, may be used.

Another, second trained function has already been trained offline to compute nuclear medical image data sets from such a first nuclear medical image data set (nuclear medical prior image) and the nuclear medical raw data set of an arbitrary or adjacent frame of the same acquisition, wherein the resulting further nuclear medical image data set corresponds to a registration and reconstruction result as used to determine the first nuclear medical image data set. In other words, since these iterative reconstruction approaches incorporating anatomical information serve to improve the quality of the nuclear medical image data sets regarding sharpness and noise, the second trained function yields a sharpened and denoised high resolution nuclear medical image data set from the results of a standard reconstruction of at least one other frame.

In this manner, a huge improvement in performance can be achieved, since no or only one computationally expensive registration and possibly analytical reconstruction need to be executed for the raw data of at least one reference frame, with all other frames of interest being processed via the second trained function. Cross-modality registration of nuclear medical data and anatomical image data in consecutive frames is no longer required. In addition, a source of uncertainty and sometimes low image quality, namely the registration, may be eliminated from the process.

In preferred embodiments, the nuclear medical raw data sets and the anatomical image are acquired using the same imaging device, in particular at least partly at the same time. Such imaging devices combining two modalities, for example PET/MRI devices, PET/CT devices, or SPECT/CT devices, have already been proposed in the art and can advantageously be applied here. Using such a combined imaging device, the anatomical image can be acquired during at least one of the frames, in particular in a predetermined, chosen frame. Since, in a combined imaging device, the coordinate systems of the nuclear medical imaging and the anatomical imaging are already registered to each other, it can be safely assumed that optimal co-registration between nuclear medical raw data and the anatomical image acquired in the same frame is already provided, such that no time-consuming multi-modality registration step is required in the inventive method. Hence, the nuclear medical imaging data sets can be determined very fast, in particular in real time. Preferably, the results of the examination may be provided immediately after the examination has been performed.

Hence, in preferred embodiments, a basis raw data set may be chosen as a single nuclear medical raw data set already co-registered to the anatomical image and/or from one single frame during which the anatomical image was acquired or closest to the acquisition of the anatomical image. The one single frame may be the first frame of the time interval, or, preferably, a frame showing a higher uptake of the tracer in the field of view, in particular a central frame. The one single frame can also be called a reference frame. It is preferably chosen to have an optimal matching to the anatomical image. For example, the first nuclear medical image data set may be determined for the first frame as the reference frame, whereafter further nuclear medical image data sets may be determined using the second trained function for the second, third, fourth, and so on frame. Herein, the respective previous result may be used as input for determining the current result, as already discussed above. In this manner, the changes regarding the respectively used nuclear medical prior image in the second trained function are minimized. However, since, in particular in dynamic studies with highly perfusive tracers, the first frame might not have meaningful image content, since very little uptake is present, and hence may not be the optimal choice for a reference frame, in such cases, it is preferred to use a central frame having a high uptake, for example based on a head curve analysis, as a reference and then determine the remaining nuclear medical image data sets relative to this central frame, for example by progressing as described above in different directions.

When the anatomical image is not acquired in one of the frames, or even with a longer time distance to the nuclear medical raw data sets, in preferred embodiments, the one single frame may also be chosen as the one where a measure indicating the quality of co-registration between the nuclear medical raw data set and the anatomical image is optimal. Hence, the one single frame may be chosen as the frame where such a measure, which may be a deviation measure, is minimal or maximal, depending on its definition. Preferably, I may be checked whether the measure is lower or high than a threshold value for the measure indicating a certain minimum quality of the co-registration which is required, wherein, if the threshold is not held, a co-registration process of the optimally co-registered nuclear medical raw data set and the anatomical image may be triggered. As the measure, for example, a mean squares measure and/or a maximum cross correlation may be used. Since different modalities are used, mutual information is preferably employed.

It is generally noted that, as dynamic studies in nuclear medical imaging are often performed in these areas, one or more example embodiments of the present invention can preferably by applied to neurological and/or perfusion imaging. Hence, a neurological and/or perfusion tracer can be imaged. In this context, but also generally, the frame duration may, for example, be ten to thirty seconds, wherein five to twenty dynamic frames may be acquired.

It is further noted that the current invention is also advantageous if co-registration of the anatomical image with any of the nuclear medical raw data is not inherently provided, for example by using a combined imaging device providing both modalities. In this case, before reconstruction of the first nuclear medical image data set, the anatomical image may be co-registered to the basis raw data set. In this manner, a time-consuming registration may have to be performed, but only once. This is already a huge improvement compared to previous approaches, in which a registration had to be performed for each of the frames.

In this context, in preferred embodiments, the basis raw data set may comprise the nuclear medical raw data sets of all frames. That is, in this case, the basis raw data set is the full count data set of the examination, in particular the time interval. In this manner, more data are available, allowing easier and more robust co-registration, for example in a case that the anatomical image has been acquired outside the time interval and/or even by another imaging device.

In preferred embodiments, the iterative reconstruction may be based on maximum likelihood expectation maximization (MLEM) and/or use a Bowsher prior. Working based on MLEM and integrating anatomical information into the reconstruction by using a Bowsher prior has proven to yield results of particular high quality, which is also advantageous as a starting point for the second trained function, which also provides sharpened and denoised high-quality and high-resolution nuclear medical image data sets, in other words Bowsher-like results. For details on these approaches, it is referred to the state of the art, regarding the first trained function in particular to the cited article by Georg Schramm et al.

In general, a trained function mimics cognitive functions that humans associate with other human minds. In particular, by training based on training data the trained function is able to adapt to new circumstances and to detect and extrapolate patterns.

In general, parameters of a trained function can be adapted via training. In particular, supervised training, semi-supervised training, unsupervised training, reinforcement learning and/or active learning can be used. Furthermore, representation learning (an alternative term is "feature learning") can be used. In particular, the parameters of the trained functions can be adapted iteratively by several steps of training.

In particular, a trained function can comprise a neural network, a support vector machine, a decision tree and/or a Bayesian network, and/or the trained function can be based on k-means clustering, Q-learning, genetic algorithms and/or association rules. In particular, a neural network can be a deep neural network, a convolutional neural network (CNN) or a convolutional deep neural network. Furthermore, a neural network can be an adversarial network, a deep adversarial network and/or a generative adversarial network (GAN).

The second trained function of the method according to one or more example embodiments of the present invention may, for example, be trained using data from previous dynamic studies as training data. In particular and preferably, second trained function may be provided by:
providing trained data sets comprising a series of training nuclear medical raw data sets of a training field of view, each training nuclear magnetic raw data set associated with different training frames of a respective training time interval, wherein the training time interval comprises a progression period of a tracer in the training field of view, and a training anatomical image of the field of view, for each training data set, determining training input data comprising:
    a first training nuclear medical image data set determined in a determination process by
    selecting at least one of the training nuclear medical raw data sets as a training basis raw data set, wherein, optionally, a training basis raw data set may be co-registered to the training anatomical image, and reconstructing the first training nuclear medical image data set by either
    iterative reconstruction of the training basis raw data set using a prior based on the, in particular co-registered, training anatomical image to incorporate anatomical information into the reconstruction process,
        or
    using the first trained function applying such an iterative reconstruction to the, preferably co-registered, training anatomical image, and the training basis raw data set and/or a preliminary reconstructed data set thereof,
    for each frame not being a single frame forming the training basis data set, the nuclear medical raw data set of the respective frame and/or a preliminary reconstructed image reconstructed therefrom,
    for each training data set, determining as training output data, for each frame not being a single frame forming the training basis raw data set, a further training output nuclear medical image data set by applying the determination process to the training nuclear medical raw data set of the respective frame as training basis raw data set.

In an alternative approach, where the second trained function should only be based on frames directly adjacent in time, pairs of training input data and training output data may be determined by using the determination process for one frame to determine the first or further training nuclear medical image data set as input data and, for the other frame, use the determination process to determine the further training nuclear medical image data set as output data. To provide additional training data, this may of course also be done vice versa, and in the variant described before, multiple frames may be choses as reference frame to generate more training data.

Of course, a corresponding computer-implemented method for providing the second trained function and/or a corresponding providing system are also conceivable.

Here, as well as in the case where co-registration of the basis raw data set and the anatomical image are performed in the determination method, multi-modality co-registration may be performed based on a preliminary, in particular backprojection, reconstruction of the basis raw data set. Multiple such registration approaches have been proposed in the state of the art, exemplarily, it can be referred to Frederik Maes et al., "Medical Image Registration Using Mutual Information", Proceedings of the IEEE, Vol. 91, No. 10, October 2003, pages 1699-1722.

It should be noted at this point that it is preferred to not use the nuclear medical raw data as input for the second trained function, but a preliminary reconstructed, for example backprojected, image, as such preliminary reconstructed images are easier to interpret for the second trained function and hence improve robustness and training performance.

Generally speaking, the first trained function may comprise a convolutional neural network and/or use a preliminary reconstructed, in particular backprojected, image and the anatomical image as input data, as, for example, proposed in the article by Georg Schramm et al. cited above. Hence, advantageously, the raw data are not needed as input for this reconstruction approach.

In preferred embodiments, the second trained function may comprise a convolutional neural network and/or a ResNet. Both options have proven to be efficient regarding the training phase as well as robust and fast in the application phase. In concrete embodiments, the convolutional neural network may comprise at least one fully connected layer and/or at least one patchwise fully connected layer. In particular, a convolutional neural network comprising only fully connected layers may be used. For example, such a convolutional neural network may comprise three to five fully connected layers and/or patchwise fully connected layers. Patchwise fully connected layers can be understood as providing local transformation processes, since the effects addressed here can also be seen as local. In particular, varying definitions of patches in the second trained function may be used for varying pairs of layers to analyze different local neighborhoods.

In especially preferred embodiments, attenuation correction may be applied based on an attenuation map, which is also used in the reconstruction of the first nuclear medical image data set. Here, the attenuation map may, for example, be used for modelling count loss by integration of attenuation along a line of response and corresponding corrections for comparison of a current estimate with the nuclear medical raw data. Attenuation correction further improves the image quality of the resulting nuclear medical image data sets. Attenuation correction approaches using attenuation maps, which are often also called p-maps, are in principle known in the art.

Preferably, the attenuation map may be determined from the anatomical image. In the case that co-registration is performed, the attenuation map is preferably determined from the co-registered anatomical image. In this manner, the attenuation map is also inherently co-registered, in particular also if co-registration was already inherently provided, for example for acquiring the basis raw data and the anatomical image in the same frame. Since the anatomical image describes the anatomy of the field of view of the patient, attenuation coefficients can be assigned to certain anatomical structures, in the case of CT images as anatomical images derived from or as image values, since CT images also describe attenuation. In the case of MRI mostly discussed here, Dixon methods are usually applied.

Regarding attenuation correction for the further nuclear medical image data sets, three different embodiments are envisioned in the current invention, which may be applicable in different cases, in particular regarding patent motion.

In a first embodiment, in particular if no relevant patient motion occurs, an attenuation-corrected preliminary reconstructed, for example backprojected, image based on the attenuation map is used as input data for the second trained function. In the absence of motion, or when only irrelevant motion is expected, the attenuation map can be used for all frames unchanged. Hence, for each frame, the attenuation map can be used to determine an attenuation-corrected preliminary reconstructed image, which, in turn, can be used as input to the second trained function, which thus does not need to incorporate the attenuation correction. Generally speaking, supplying already attenuation-corrected input data to the second trained function allows a more efficient learning procedure, since less correlations have to be learned.

If, however, motion by the patient is expected or present, the second or third concrete embodiments in this context can advantageously be used. In the second concrete embodiment regarding attenuation correction, in the case of patient motion, a corrected attenuation map is determined for each frame, to which the second trained function is to be applied, by determining correction parameters from not attenuation-corrected preliminary reconstructed images of the relevant frames and correcting the attenuation map according to the correction parameters, wherein an attenuation-corrected preliminary reconstructed image based on the respective corrected attenuation map is used as input data for the second trained function. In principle, such correction parameters describing motion are registration parameters between not attenuation-corrected preliminary reconstructed images (NAC images) of the frames, which may be applied to the attenuation map. The corrected attenuation map may then serve as input to the preliminary attenuation-corrected reconstruction, the result of which, that is the attenuation-corrected preliminary reconstructed image (AC image), may be used as input to the second trained function. It is noted that, in this context, it is preferred to register the NAC images of neighboring frames to determine the correction parameters, since, here, only little motion is expected compared to longer time spans. While, in particular and as described above, the pairs of NAC images to determine correction parameters may be chosen according to the frames from which input data is used in the second trained function, such that neighboring frames may be used both for correcting the attenuation map and for determining the further nuclear medical image data set, it is, of course, also possible to choose different pairs of frames for the input to the second trained function and the determination of the correction parameters, as long as corrected attenuation maps for all relevant frames are determined.

In a third concrete embodiment regarding attenuation correction, it is also possible to train the second trained function to also learn the attenuation correction, which may require more training data, but allows to skip a correction process in the case of motion of the patient. That is, the attenuation map is only used for determining the first nuclear medical image data set, wherein a not attenuation-corrected preliminary reconstructed image is used as input data for the second trained function.

In advantageous embodiments, the nuclear medical raw data sets may be PET raw data sets and/or the anatomical image may be a magnetic resonance image. Experiments have shown that one or more example embodiments of the present invention is especially advantageously applicable to the PET/MRI combination, while other applications are also advantageously possible. For example, CT images have also been proposed as carrying useful anatomical information which may be incorporated into the reconstruction process. Furthermore, dynamic studies have also been proposed for SPECT, such that the current invention can also be applied to these examinations.

One or more example embodiments of the present invention further concerns a determining device for determining nuclear medical image data sets in dynamic nuclear medical imaging, comprising:

a first interface for providing nuclear medical raw data sets of a field of view acquired over a time interval, wherein the time interval comprises a progression period of the tracer in the field of view and each nuclear medical raw data set is acquired in one of multiple time frames, into which the time interval is divided, a second interface for providing an anatomical image showing the anatomy in the field of view, a selection unit for selecting at least one of the nuclear medical raw data sets as a basis raw data set, a reconstruction unit for reconstructing a first nuclear medical image data set by either iterative reconstruction of the basis raw data set using a prior based on the anatomical image to incorporate anatomical information, or using a first trained function applying such an iterative reconstruction to the anatomical image, and the basis raw data set and/or a preliminary reconstructed data set thereof, a determination unit using a second trained function to determine at least one further nuclear medical image data set for, if the basis raw data set is taken from one single frame, at least one other frame, in particular all other frames, else, at least one frame, in particular all frames, as output data, wherein input data of the second trained function comprises the nuclear medical raw data set of the respective frame and/or a preliminary reconstructed image reconstructed therefrom, and an already determined nuclear medical image data set, and a third interface for outputting at least the at least one further nuclear medical image data set.

Of course, if the first nuclear medical image data set refers to a single frame, it will also be output via the third interface; also first nuclear medical image data sets based on raw data of multiple frames, in particular all frames, may of course be output if they are of any value for the evaluation.

Generally speaking, the determining device may comprise at least one processor and/or a storage means and is configured to perform a method according to one or more example embodiments of the present invention. All features and remarks discussed regarding the method according to one or more example embodiments of the present invention can be analogously applied to the determining device according to one or more example embodiments of the present invention and vice versa. In particular, further functional units may be provided to implement additional, optional steps. For example, in embodiments, the determining device may additionally comprise a registration unit for co-registering the anatomical image to the basis raw data set.

In some embodiments, the determining device may be integrated into an imaging device, preferably into a combined imaging device providing both the nuclear medical imaging modality and the anatomical imaging modality. For example, such a combined imaging device, in particular a PET/MRI device or a PET/CT device, is conceivable, wherein the control device of the combined imaging device comprises a determining device according to one or more example embodiments of the present invention.

A computer program according to one or more example embodiments of the present invention can be directly loaded into a determining device and enables the determining device to perform the steps of a method according to one or more example embodiments of the present invention when the computer program is executed on the determining device. The computer program according to one or more example embodiments of the present invention may be stored on an electronically readable storage medium according to one or more example embodiments of the present invention, which thus comprises control information comprising a computer program according to one or more example embodiments of the present invention such that, when the electronically readable storage medium is used in a determining device, the determining device is configured to perform the steps of a method according to one or more example embodiments of the present invention when the computer program according to one or more example embodiments of the present invention is executed in the determining device. The electronically readable storage medium according to one or more example embodiments of the present invention may preferably be a non-transitory medium, for example a CD ROM.

FIG. 1 displays an embodiment of an artificial neural network 1. Alternative terms for "artificial neural network" are "neural network", "artificial neural net" or "neural net".

The artificial neural network 1 comprises nodes 6-18 and edges 19-21, wherein each edge 19-21 is a directed connection from a first node 6-18 to a second node 6-18. In general, the first node 6-18 and the second node 6-18 are different nodes 6-18. It is also possible that the first node 6-18 and the second node 6-18 are identical. For example, in FIG. 1 the edge 19 is a directed connection from the node 6 to the node 9, and the edge 20 is a directed connection from the node 7 to the node 9. An edge 19-21 from a first node 6-18 to a second node 6-18 is also denoted as "ingoing edge" for the second node 6-18 and as "outgoing edge" for the first node 6-18.

In this embodiment, the nodes 6-18 of the artificial neural network 1 can be arranged in layers 2-5, wherein the layers 2-5 can comprise an intrinsic order introduced by the edges 19-21 between the nodes 6-18. In particular, edges 19-21 can exist only between neighboring layers of nodes 6-18. In the displayed embodiment, there is an input layer 2 comprising only nodes 6-8 without an incoming edge, an output layer 5 comprising only nodes 17, 18 without outgoing edges, and hidden layers 3, 4 in-between the input layer 2 and the output layer 5. In general, the number of hidden layers 3, 4 can be chosen arbitrarily. The number of nodes 6-8 within the input layer 2 usually relates to the number of input values of the neural network, and the number of nodes 17, 18 within the output layer 5 usually relates to the number of output values of the neural network.

In particular, a (real) number can be assigned as a value to every node 6-18 of the neural network 1. Here, x(n)i denotes the value of the i-th node 6-18 of the n-th layer 2-5. The values of the nodes 6-8 of the input layer 2 are equivalent to the input values of the neural network 1, the values of the nodes 17, 18 of the output layer 5 are equivalent to the output values of the neural network 1. Furthermore, each edge 19-21 can comprise a weight being a real number, in particular, the weight is a real number within the interval [−1, 1] or within the interval [0, 1]. Here, w(m,n)i,j denotes the weight of the edge between the i-th node 6-18 of the m-th layer 2-5 and the j-th node 6-18 of the n-th layer 2-5. Furthermore, the abbreviation w(n)i,j is defined for the weight w(n,n+1)i,j.

In particular, to calculate the output values of the neural network 1, the input values are propagated through the neural network 1. In particular, the values of the nodes 6-18 of the (n+1)-th layer 2-5 can be calculated based on the values of the nodes 6-18 of the n-th layer 2-5 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network 1, wherein values of the input layer 2 are given by the input of the neural network 1, wherein values of the first hidden layer 3 can be calculated based on the values of the input layer 2 of the neural network 1, wherein values of the second hidden layer 4 can be calculated based in the values of the first hidden layer 3, etc.

In order to set the values w(m,n)i,j for the edges 19-21, the neural network 1 has to be trained using training data. In particular, training data comprises training input data and training output data (denoted as ti). For a training step, the neural network 1 is applied to the training input data to generate calculated output data. In particular, the training data and the calculated output data comprise a number of values, said number being equal to the number of nodes 17, 18 of the output layer 5.

In particular, a comparison between the calculated output data and the training data is used to recursively adapt the weights within the neural network 1 (backpropagation algorithm). In particular, the weights are changed according to $$w'^{(n)}_{i,j} = w_{i,j}^{(n)} - \gamma \cdot \delta_j^{(n)} \cdot x_i^{(n)}$$

wherein γ is a learning rate, and the numbers δ(n)j can be recursively calculated as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on δ(n+1)j, if the (n+1)-th layer is not the output layer 5, and $$\delta_j^{(n)} = (x_k^{(n+1)} - t_j^{(n+1)}) \cdot f'(\Sigma_i x_i^{(n)} \cdot w_{i,j}^{(n)})$$

if the (n+1)-th layer is the output layer 5, wherein f' is the first derivative of the activation function, and y(n+1)j is the comparison training value for the j-th node of the output layer 5.

Figure 2:
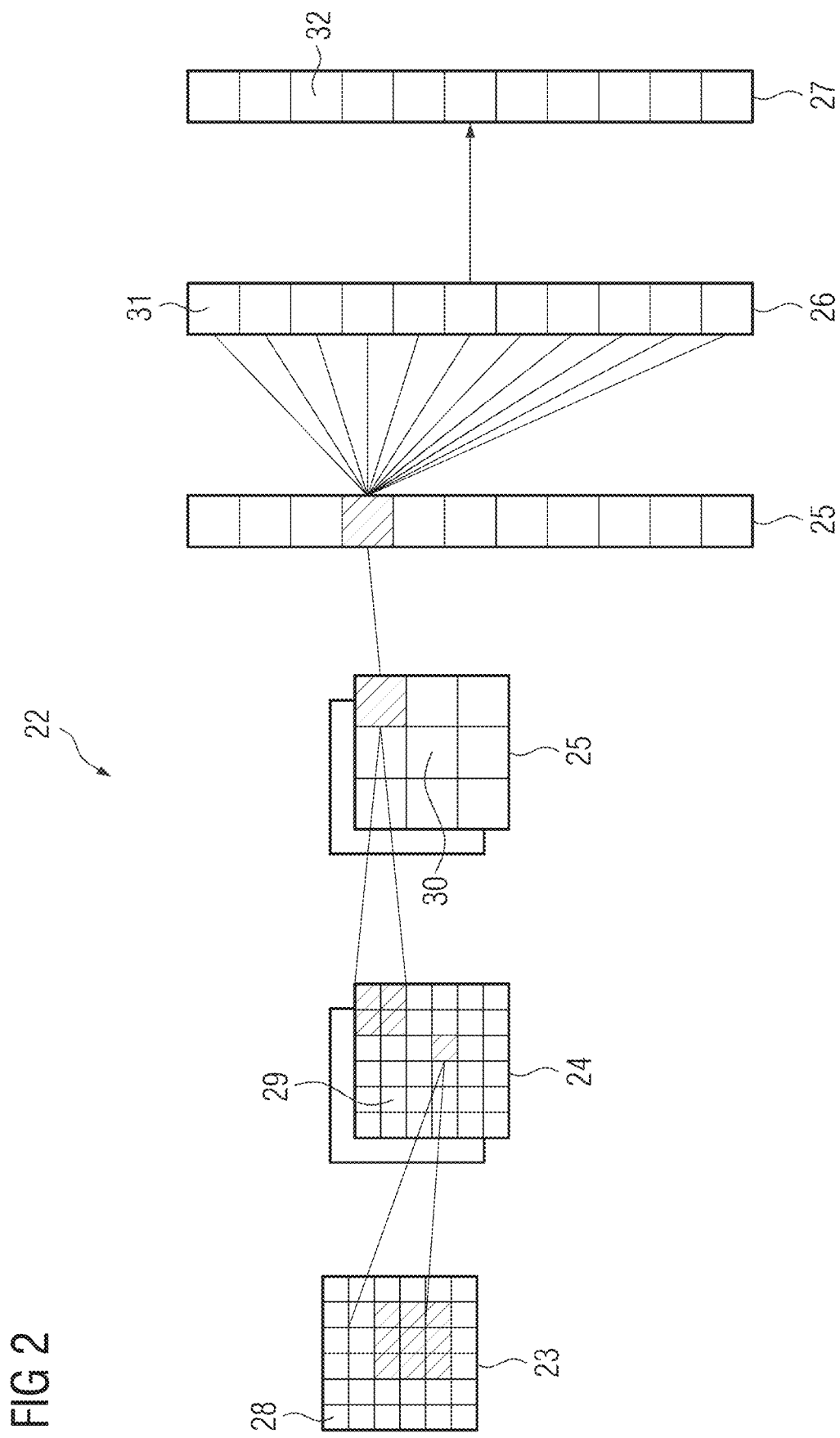

FIG. 2 displays an embodiment of a convolutional neural network 22. In the displayed embodiment, the convolutional neural network 22 comprises an input layer 23, a convolutional layer 24, a pooling layer 25, a fully connected layer 26 and an output layer 27. Alternatively, the convolutional neural network 22 can comprise several convolutional layers 24, several pooling layers 25 and several fully connected layers 26 as well as other types of layers. The order of the layers can be chosen arbitrarily, usually fully connected layers 26 are used as the last layers before the output layer 27.

In particular, within a convolutional neural network 22 the nodes 28-32 of one layer 23-27 can be considered to be arranged as a d-dimensional matrix or as a d-dimensional image. In particular, in the two-dimensional case the value of the node 28-32 indexed with i and j in the n-th layer 23-27 can be denoted as x(n) [i,j]. However, the arrangement of the nodes 28-32 of one layer 23-27 does not have an effect on the calculations executed within the convolutional neural network 22 as such, since these are given solely by the structure and the weights of the edges.

In particular, a convolutional layer 24 is characterized by the structure and the weights of the incoming edges forming a convolution operation based on a certain number of kernels. In particular, the structure and the weights of the incoming edges are chosen such that the values x(n)k of the nodes 29 of the convolutional layer 24 are calculated as a convolution x(n)k=Kk*x(n−1) based on the values x(n−1) of the nodes 28 of the preceding layer 23, where the convolution * is defined in the two-dimensional case as $$x_k^{(n)}[i,j]=(K_k*x^{(n-1)})[i,j]=\Sigma_i\Sigma_j K_k[i',j']\cdot x^{(n-1)}[i-i',j-j'].$$

Here the k-th kernel Kk is a d-dimensional matrix (in this embodiment a two-dimensional matrix), which is usually small compared to the number of nodes 28-32 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 28-32 in the respective layer 23-27. In particular, for a convolutional layer 24 the number of nodes 29 in the convolutional layer is equivalent to the number of nodes 28 in the preceding layer 23 multiplied with the number of kernels.

If the nodes 28 of the preceding layer 23 are arranged as a d-dimensional matrix, using a plurality of kernels can be interpreted as adding a further dimension (denoted as "depth" dimension), so that the nodes 29 of the convolutional layer 24 are arranged as a (d+1)-dimensional matrix. If the nodes 28 of the preceding layer 23 are already arranged as a (d+1)-dimensional matrix comprising a depth dimension, using a plurality of kernels can be interpreted as expanding along the depth dimension, so that the nodes 29 of the convolutional layer 64 are arranged also as a (d+1)-dimensional matrix, wherein the size of the (d+1)-dimensional matrix with respect to the depth dimension is by a factor of the number of kernels larger than in the preceding layer 23.

The advantage of using convolutional layers 24 is that spatially local correlation of the input data can exploited by enforcing a local connectivity pattern between nodes of adjacent layers, in particular by each node being connected to only a small region of the nodes of the preceding layer.

In the displayed embodiment, the input layer 23 comprises 36 nodes 28, arranged as a two-dimensional 6×6 matrix. The convolutional layer 24 comprises 72 nodes 29, arranged as two two-dimensional 6×6 matrices, each of the two matrices being the result of a convolution of the values of the input layer 23 with a kernel. Equivalently, the nodes 29 of the convolutional layer 24 can be interpreted as arranged as a three-dimensional 6×6×2 matrix, wherein the last dimension is the depth dimension.

A pooling layer 25 can be characterized by the structure and the weights of the incoming edges and the activation function of its nodes 30 forming a pooling operation based on a non-linear pooling function f. For example, in the two-dimensional case the values x(n) of the nodes 30 of the pooling layer 25 can be calculated based on the values x(n−1) of the nodes 29 of the preceding layer 24 as $$x^{(n)}[i,j]=f(x^{(n-1)}[id_1,jd_2],\ldots,x^{(n-1)}[id_1+d_1-1,jd_2+d_2-1])$$

In other words, by using a pooling layer 25 the number of nodes 29, 30 can be reduced, by replacing a number d1·d2 of neighboring nodes 29 in the preceding layer 24 with a single node 30 being calculated as a function of the values of said number of neighboring nodes in the pooling layer 25. In particular, the pooling function f can be the max-function, the average or the L2-Norm. In particular, for a pooling layer 25 the weights of the incoming edges are fixed and are not modified by training.

The advantage of using a pooling layer 25 is that the number of nodes 29, 30 and the number of parameters is reduced. This leads to the amount of computation in the network 22 being reduced and to a control of overfitting.

In the displayed embodiment, the pooling layer 25 is a max-pooling, replacing four neighboring nodes with only one node, the value being the maximum of the values of the four neighboring nodes. The max-pooling is applied to each d-dimensional matrix of the previous layer 24; in this embodiment, the max-pooling is applied to each of the two two-dimensional matrices, reducing the number of nodes from 72 to 18.

A fully-connected layer 26 can be characterized by the fact that a majority, in particular, all edges between nodes 30 of the previous layer 25 and the nodes 31 of the fully-connected layer 26 are present, and wherein the weight of each of the edges can be adjusted individually.

In this embodiment, the nodes 30 of the preceding layer 25 of the fully-connected layer 26 are displayed both as two-dimensional matrices, and additionally as non-related nodes (indicated as a line of nodes, wherein the number of nodes was reduced for a better presentability). In this embodiment, the number of nodes 31 in the fully connected layer 26 is equal to the number of nodes 30 in the preceding layer 25. Alternatively, the number of nodes 30, 31 can differ.

Furthermore, in this embodiment the values of the nodes 32 of the output layer 27 are determined by applying the Softmax function onto the values of the nodes 31 of the preceding layer 26. By applying the Softmax function, the sum of the values of all nodes 32 of the output layer 27 is 1, and all values of all nodes 32 of the output layer 27 are real numbers between 0 and 1. In particular, if using the convolutional neural network 22 for categorizing input data, the values of the output layer can be interpreted as the probability of the input data falling into one of the different categories.

A convolutional neural network 22 can also comprise a ReLU (acronym for "rectified linear units") layer. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer. Examples for rectifying functions are f(x)=max(0,x), the tangent hyperbolics function or the sigmoid function.

In particular, convolutional neural networks 22 can be trained based on the backpropagation algorithm. For preventing overfitting, methods of regularization can be used, e.g. dropout of nodes 28-32, stochastic pooling, use of artificial data, weight decay based on the L1 or the L2 norm, or max norm constraints.

FIG. 3 is a general flowchart for embodiments of a method according to the invention. Generally, the method concerns generating nuclear medical image data sets for different frames in a dynamic nuclear medical imaging study. Here, the propagation of the tracer, for example a neurological and/or perfusion tracer, in a field of view is imaged in a time-resolved way. Hence, the time interval for imaging spans a progression period of the tracer in the field of view, which may, for example, comprise the brain of a patient. The time interval is divided into multiple frames, for example five to twenty frames, such that, for each frame, a nuclear medical raw data set is acquired. To be able to incorporate anatomical information into the reconstruction process, preferably during one of the frames or at least in close temporal neighborhood to the time interval, an anatomical image showing the anatomy in the field of view is also acquired, for example an magnetic resonance (MR) image and/or a computational tomography (CT) image.

In a step S1, the nuclear medical raw data sets for all the frames and the anatomical image are provided via first and second interfaces of a determining device performing the method. Additionally, an attenuation map may be provided or preferably derived from the anatomical image, such that attenuation correction can also be performed in the method. However, attenuation correction will be discussed in detail with respect to the concrete embodiments of FIGS. 5 to 7.

If the determining device is integrated into a control device of a, preferably combined (hybrid), imaging device, which hence preferably provides both the modalities for nuclear medical imaging as well as for anatomical imaging, the first and second interfaces may be internal, for example to respective acquisition units controlling the acquisition of the nuclear medical raw data and the anatomical image.

In a step S2, at least one, preferably exactly one, of the frames is selected such that its nuclear medical raw data forms a basis raw data set. For example, and as for simplicity shown in the concrete embodiments, the first frame can be selected as the one single frame for the basis raw data set; however, when certain tracers are used, the uptake may still be low in the first frame, so that, alternatively, a central frame having a higher uptake may be chosen as the one single frame. Here, of course, the embodiments shown exemplarily for the first frame can analogously be applied.

The one single frame is preferably chosen such that its nuclear medical raw data set is already co-registered with the anatomical image. For example, in a combined imaging device allowing synchronous imaging for both modalities, the anatomical image may be acquired during one of the frames, such that the respective frame can be chosen as the one single frame for the basis raw data set. Regarding a high uptake, acquisition may be dedicatedly controlled to have the anatomical image acquired in such a high uptake frame. In cases where the anatomical image is acquired, in particular immediately, before the first frame or after the last frame, the first or respectively last frame may be chosen as the one single frame to be used for the basis raw data set.

In particular in a case where the anatomical image is not acquired in one of the frames, the one single frame may be chosen as the one where co-registration is already optimal. In concrete embodiments, a measure indicating the quality of co-registration already existent between respective nuclear medical raw data sets and the anatomical image may be determined and the one single frame may be chosen as the frame where this measure, which may be a deviation measure, is minimal or maximal, depending on its definition. Preferably, there may additionally be a threshold value for the measure indicating a certain minimum quality of the co-registration which is required. As such a measure, for example, a mean squares measure and/or a maximum cross correlation may be used. Since different modalities are used, mutual information is preferably employed.

In a case where sufficiently precise co-registration between the basis raw data set and the anatomical image already exists, advantageously, no cross-modality co-registration, which would be very time consuming, is relevant, and, as will become apparent, the method described here provides the nuclear medical image data sets very fast, in particular in real-time.

In some embodiments, however, an optional co-registration step S3 may be provided or possible, but less preferred. For example, if the threshold for the measure discussed above is exceeded, co-registration may be automatically prompted. In other cases, for example, if the time between the acquisition of the anatomical image and the nuclear medical raw data is very long, co-registration in a step S3 may generally be required. However, as will become apparent, in comparison to the state of the art, multi-modality co-registration has to be performed at most once, as opposed to the state of the art, where it had to be performed once for each frame.

In a step S4, iterative reconstruction, in particular MLEM reconstruction, is applied using a prior based on the anatomical image, wherein the co-registration between the anatomical image and the basis raw data set is exploited. Preferably, the iterative registration applied is based on a Bowsher prior. In step S4, the iterative reconstruction may be performed analytically, however, regarding computational effort, a first trained function modelling the iterative reconstruction (and thus applying it implicitly) may be used, for example as described in the cited articles by D. Rigio et al. and Georg Schramm et al.

As a result of step S4, a first nuclear medical image data set is determined, which, if the basis raw data is taken from one single frame, also forms the result image for this frame. However, it should be noted that in some cases, more frames may be included into the basis raw data set, in particular all frames, such that the result would be a full-count nuclear medical image for the time interval.

In step S5, for all other frames for which a denoised and sharpened reconstruction is required, a second trained function is applied. The second trained function has been trained to use input data comprising an already reconstructed nuclear medical image data set as well as data from the respective frame as input to derive the reconstructed nuclear medical image data set for the respective frame therefrom. Here, for training, previously acquired data from dynamic studies may be employed. In particular, for the first application of the second trained function, of course, the first nuclear medical image data set has to be used. While it is in principle possible to use the first nuclear medical image data set for all the frames to be reconstructed, in preferred embodiments as discussed here, the second trained function is in particular trained to derive the nuclear medical image data set for a certain frame from the result of a neighboring frame. That is, if the first frame is the one single frame for the basis raw data set, the second frame is next reconstructed using the result for the first frame derived in step S4. After that, the third frame is reconstructed using the result of the second frame, and so on. If a central frame (i.e., not the first or last frame) has been chosen in step S2, propagation may be conducted in both time directions starting from the central frame.

In preferred embodiments, a preliminary reconstructed, in particular backprojected, image is used as input data from the respective frame, as will be further discussed below.

However, embodiments are conceivable, in which the respective nuclear medical raw data set is used.

Preferably, in this manner, nuclear medical image data sets showing high-resolution high-quality distributions of the tracer in the respective frames are determined for each frame. In particular, when using the first trained function as well as the second trained function, result images for all frames may be provided in real time.

In a step S6, the resulting nuclear medical image data sets may be output, for example for further evaluation, storing in a picture archive and/or displaying to a user.

FIG. 4 shows an exemplary structure of the second trained function 33 used in step S5. Here, as the second trained function 33, a convolutional neural network 22 is used, which comprises an input layer 23, a series of fully connected layers 26 and/or patchwise fully connected layers 26 and an output layer 27. For example, three to ten fully connected layers and/or patchwise fully connected layers 26 can be used. In alternative embodiments, other layers may be additionally employed and/or a ResNet may be used instead of a CNN 22. The use of patchwise fully connected layers 26 advantageously incorporates the knowledge that the changes from frame to frame are mostly local effects.

In the following, three concrete embodiments will be discussed, in particular to illustrate possibilities to incorporate attenuation correction. These examples are preferably applied to PET imaging as nuclear medical imaging and magnetic resonance images as anatomical images, but may, of course, also be applied for other modalities.

Figure 5:
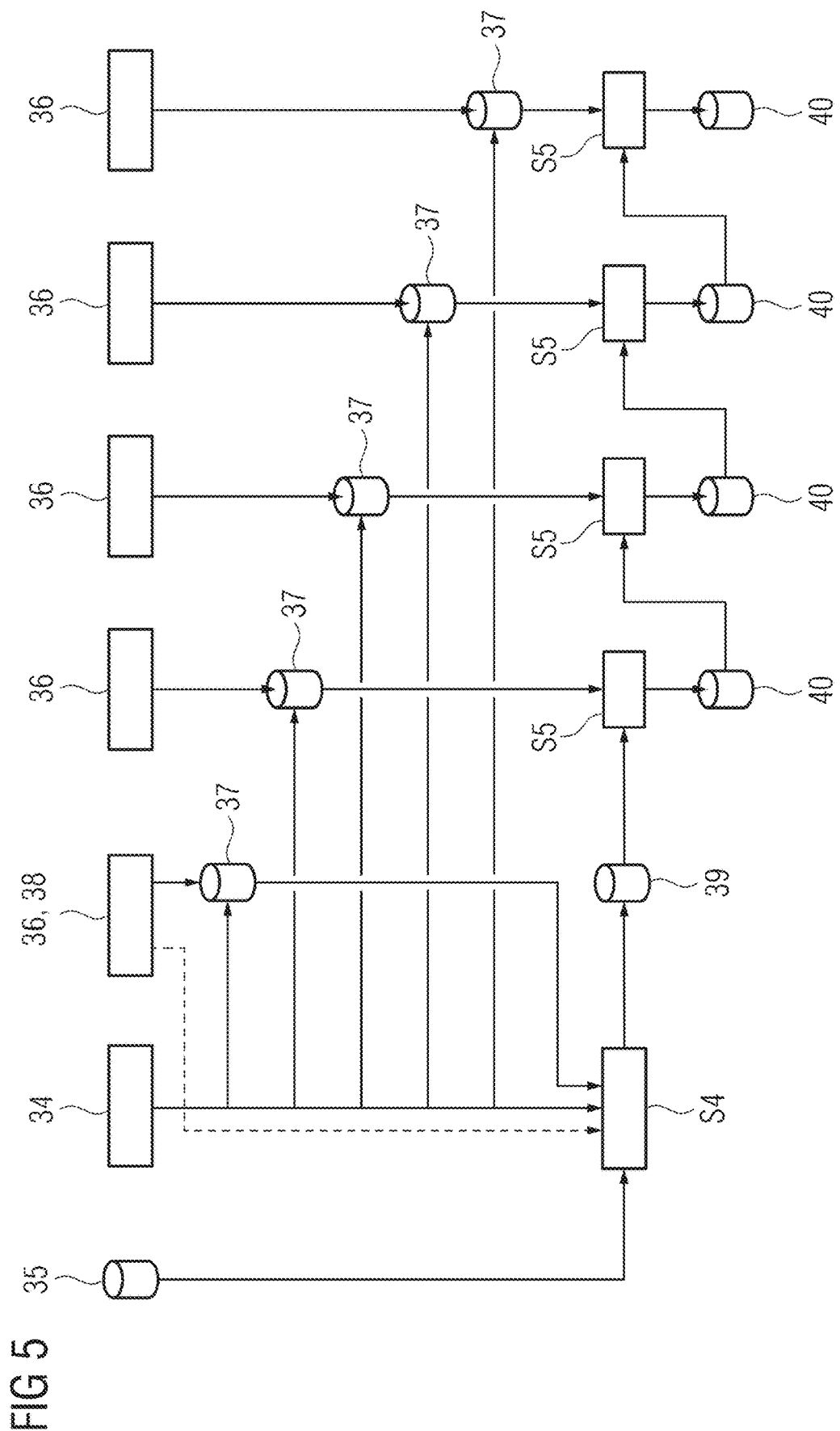

In a first embodiment shown in FIG. 5, no (relevant) patient motion occurs, such that an attenuation map 34, preferably derived from the anatomical image 35, can be used for attenuation correction in all frames. Hence, for each nuclear medical raw data set 36 the attenuation map 34 is used to determine an attenuation corrected preliminary reconstructed, here backprojected, image 37 (AC image) that can be used as input data for steps S4, S5 respectively. For example, in the case of an MR image, a Dixon technique could be used to acquire it, such that an attenuation map can be derived from it based in the different material classes distinguished. It is noted that the attenuation map 34 is also used in step S4, since modelling the forward projection requires attenuation knowledge to allow correct comparison between forward projected data and nuclear medical raw data.

It is noted that, if a first trained function is used in step S4, it may not be necessary to also supply the respective basis raw data to the first trained function as input data, but only a preliminary backprojected image 37. Furthermore, in these embodiments, for simplicity of presentation, the first frame is always shown as the one single frame for the basis raw data set 38, which then is the nuclear medical raw data set 36 of the first frame. However, it is apparent to the person skilled in the art that these embodiments may be analogously transferred to other frames as the single one frame.

As shown in FIG. 5, for the first frame, the first nuclear medical image data set 39 is determined as result of the step S4. For all further frames, as shown, the previously determined first nuclear medical image data set 39 or further nuclear medical image data set 40 together with the NAC images 37 is used as input data for the second trained function 33 in step S5, such that, finally, nuclear medical image data sets 39, 40 have been determined for all frames, wherein attenuation correction has already been applied during or after preliminary backprojection.

Figure 6:
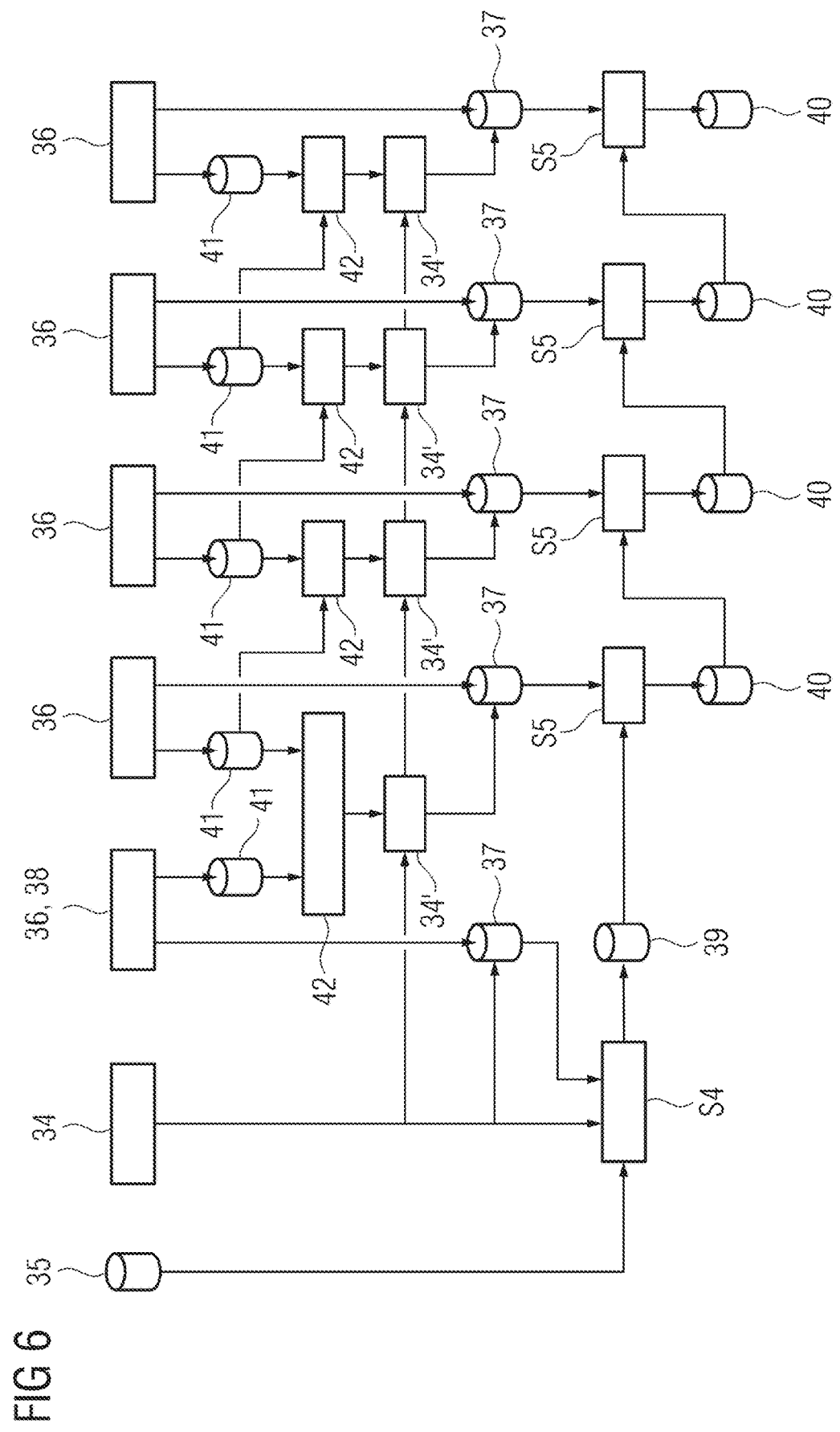
Figure 7:
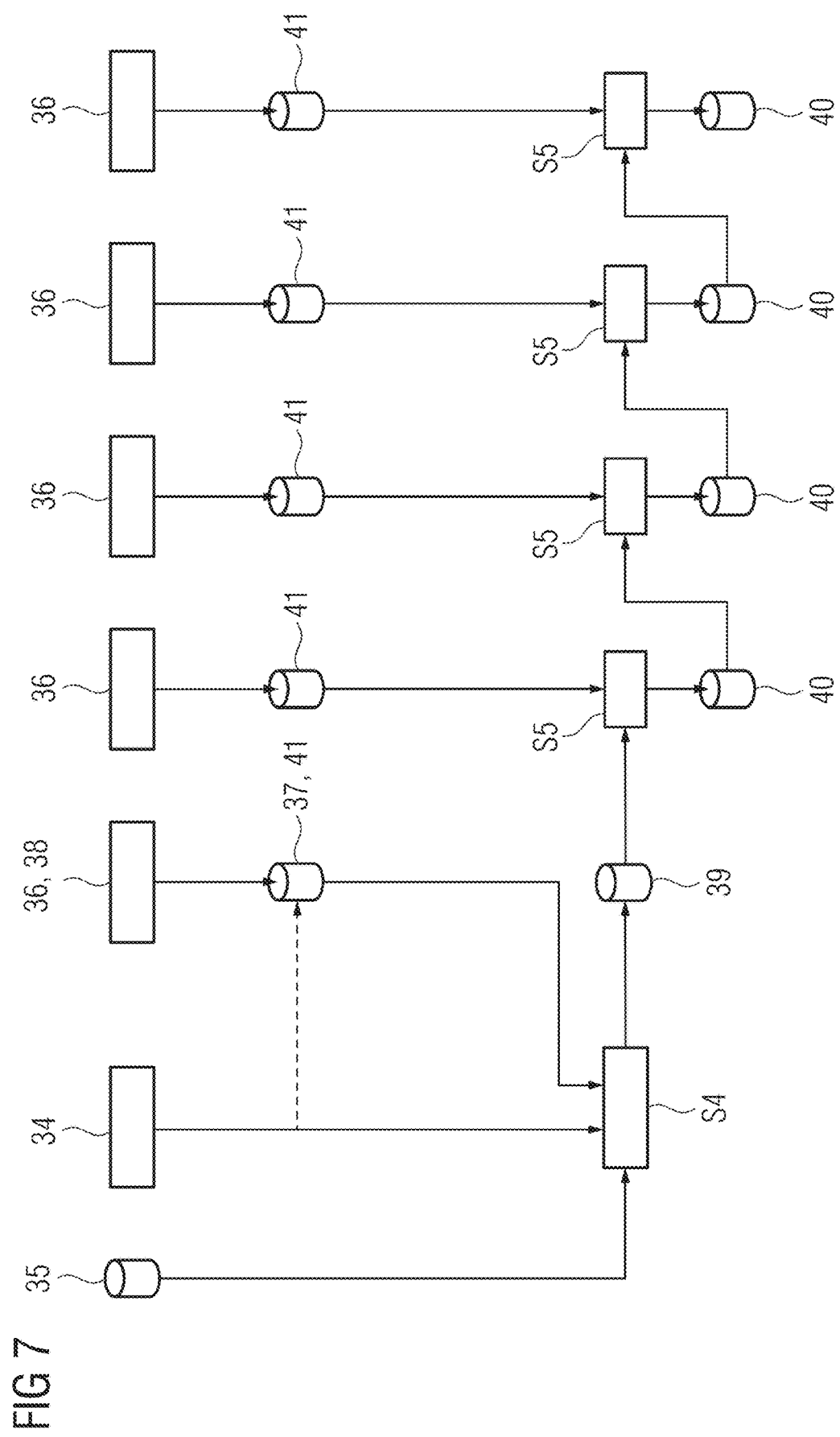

The second and third embodiments shown in FIGS. 6 and 7 refer to patient motion occurring during the time interval.

A first approach to attenuation correction in this case is shown in FIG. 6, where, again, the first frame is used for the basis raw data set 38 and optimally registered to the anatomical image 35, from which the attenuation map 34 is derived. Hence, the attenuation map 34 can again be used to determine an attenuation-corrected preliminary backprojected image 37 for the first frame. For later frames, in these embodiments, non-attenuation-corrected preliminary backprojected images 41 (NAC images) are determined for each frame from the respective nuclear medical raw data sets 36 and registered between frames adjacent in time to yield correction parameters 42 (registration parameters). These correction parameters 42 describing the motion occurring between the frames is used to determine corrected attenuation maps 34' for each frame, which can be used to determine the respective AC images 37. These AC images 37 are, again, used in addition to the result of the previous frame as input data to the second trained function 33 in steps S5.

In the third embodiment according to FIG. 7, the second trained function 33 has also been trained to perform attenuation correction, such that NAC images 41 may be used as input data to the second trained function 33 in step S5. Here, the attenuation map 34 is only used in step S4, and, optionally, to determine an AC image 37 if required in step S4.

Figure 8:
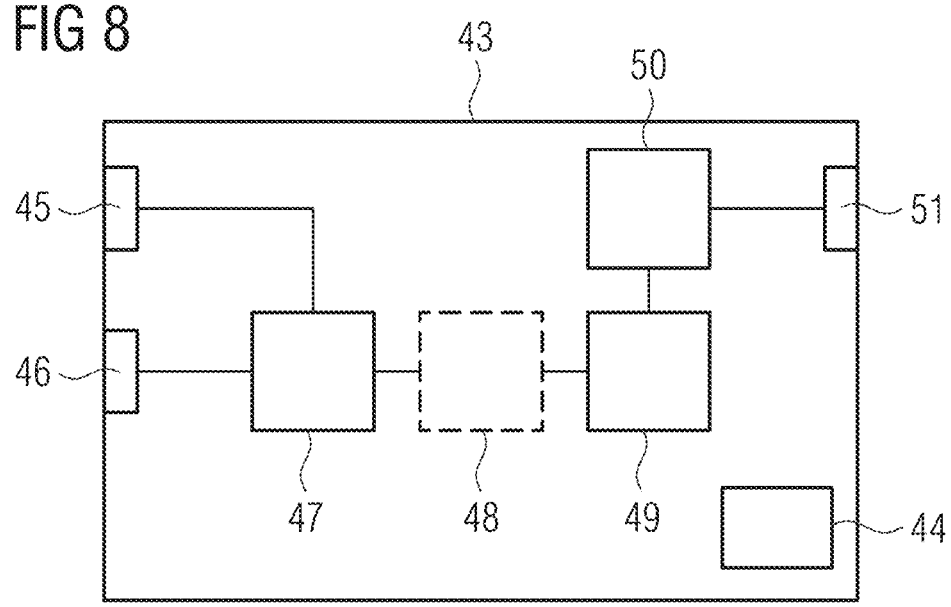

FIG. 8 shows the functional structure of a determining device 43 according to one or more example embodiments of the present invention, which may comprise of a storage means 44 for storing input information, intermediate results and/or final results. The nuclear medical raw data sets 36 are provided via a first interface 45, while the anatomical image 35 is provided via a second interface 46 (step S1). In a selection unit 47, the basis raw data set 38 is defined as discussed with respect to step S2. Optionally, a registration unit 48 may be provided for co-registration (step S3). In a reconstruction unit 49, the first nuclear medical image data set 39 can be determined according to step S4. Further nuclear medical image data sets 40 are determined according to step S5 in a determination unit 50. The resulting nuclear medical image data sets 39, 40 can be output via a third interface 51.

It is noted that the determining device 43, in particular if results can be determined at least substantially in real time, may also be integrated into the control device of a combined imaging device providing both nuclear medical imaging, in particular PET imaging, and anatomical imaging, in particular magnetic resonance imaging (MRI). Then, the interfaces 45, 46 and 51 may be internal interfaces, wherein the control device may additionally comprise acquisition units for acquiring the nuclear medical raw data sets 36 and the anatomical image 35. In particular, the acquisition units may be controlled such that, if synchronous imaging is possible, the anatomical image 35 is acquired in a certain frame of the time interval, which is then chosen as the one single frame to define the basis raw data set 38.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein and mentioned above, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing system or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAN), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium, storage means or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the nontransitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been described in detail with reference to the preferred embodiment, the present invention is not limited by the disclosed examples from which the skilled person is able to derive other variations without departing from the scope of the invention.

The invention claimed is:

1. A computer-implemented method for determining nuclear medical image data sets in dynamic nuclear medical imaging, the method comprising:
   providing nuclear medical raw data sets of a field of view acquired over a time interval, wherein the time interval comprises a progression period of a tracer in the field of view and each nuclear medical raw data set is acquired in one of multiple time frames of the time interval;
   providing an anatomical image showing an anatomy in the field of view;
   selecting at least one of the nuclear medical raw data sets as a basis raw data set;
   reconstructing a first nuclear medical image data set by
      iterative reconstruction of the basis raw data set based on the anatomical image to incorporate anatomical information, or
      using a first trained function applying the iterative reconstruction to the anatomical image and at least one of the basis raw data set or a preliminary reconstructed data set of the basis raw data set; and
   using a second trained function to determine at least one further nuclear medical image data set for,
      at least one other frame if the basis raw data set is taken from one single frame, wherein input data of the second trained function includes,
         at least one of the nuclear medical raw data set of the respective frame or a preliminary reconstructed image reconstructed therefrom, and
         an already determined nuclear medical image data set.

2. The method of claim 1, further comprising:
   selecting the basis raw data set as a single nuclear medical raw data set already at least one of (i) co-registered to the anatomical image or (ii) from one single frame during which the anatomical image was acquired or closest to the acquisition of the anatomical image.

3. The method of claim 1, wherein the basis raw data set comprises the nuclear medical raw data sets of all frames.

4. The method of claim 1, wherein the iterative reconstruction at least one of (i) is based on a maximum likelihood expectation maximization or (ii) uses a Bowsher prior.

5. The method of claim 1, wherein the first trained function at least one of (i) comprises a convolutional neural network or (ii) uses a preliminary reconstructed image and the anatomical image as input data.

6. The method of claim 1, wherein the second trained function comprises at least one of a convolutional neural network or a residual network (ResNet).

7. The method of claim 1, further comprising:
   applying attenuation correction based on an attenuation map, the attenuation correction being used in the reconstruction of the first nuclear medical image data set.

8. The method of claim 7, wherein the applying the attenuation correction includes,
   determining the attenuation map from the anatomical image.

9. The method of claim 7, wherein the input data for the second trained function further includes an attenuation-corrected preliminary reconstructed image based on the attenuation map.

10. The method of claim 7, wherein
    in a case of patient motion, a corrected attenuation map is determined for each frame, to which the second trained function is to be applied, by determining correction parameters from not attenuation corrected preliminary reconstructed images of relevant frames and correcting the attenuation map according to the correction parameters, and
    the input data for the second trained function includes an attenuation-corrected preliminary reconstructed image based on the respective corrected attenuation map.

11. The method of claim 7, wherein the attenuation map is only used for determining the first nuclear medical image data set and the input data for the second trained function includes a not attenuation-corrected preliminary reconstructed image.

12. The method of claim 1, wherein at least one of the nuclear medical raw data sets are PET raw data sets or the anatomical image is a magnetic resonance image.

13. A determining device for determining nuclear medical image data sets in dynamic nuclear medical imaging, comprising:
    a first interface configured to provide nuclear medical raw data sets of a field of view acquired over a time interval, wherein the time interval comprises a progression period of a tracer in the field of view and each nuclear medical raw data set is acquired in one of multiple time frames of the time interval;
    a second interface configured to provide an anatomical image showing an anatomy in the field of view;
    a selection unit configured to select at least one of the nuclear medical raw data sets as a basis raw data set;
    a reconstruction unit configured to reconstruct a first nuclear medical image data set by
       iterative reconstruction of the basis raw data set based on the anatomical image to incorporate anatomical information, or
       using a first trained function applying the iterative reconstruction to the anatomical image and at least one of the basis raw data set or a preliminary reconstructed data set of the basis raw data set;
    a determination unit configured to use a second trained function to determine at least one further nuclear medical image data set for,
       at least one other frame if the basis raw data set is taken from one single frame, wherein input data of the second trained function includes,
          at least one of the nuclear medical raw data set of the respective frame or a preliminary reconstructed image reconstructed therefrom, and
          an already determined nuclear medical image data set; and
    a third interface configured to output at least the at least one further nuclear medical image data set.

14. A non-transitory electronically readable storage medium including instructions that, when executed by a determining device of a system, cause the system to perform the method of claim 1.

15. A non-transitory electronically readable storage medium including instructions that, when executed by a determining device of a system, cause the system to perform the method of claim 2.

16. The method of claim 5, further comprising:
applying attenuation correction based on an attenuation map, the attenuation correction being used in the reconstruction of the first nuclear medical image data set.

17. The method of claim 16, wherein the applying the attenuation correction includes,
determining the attenuation map from the anatomical image.

18. The method of claim 16, wherein the input data for the second trained function further includes an attenuation-corrected preliminary reconstructed image based on the attenuation map.

19. The method of claim 16, wherein
in a case of patient motion, a corrected attenuation map is determined for each frame, to which the second trained function is to be applied, by determining correction parameters from not attenuation corrected preliminary reconstructed images of relevant frames and correcting the attenuation map according to the correction parameters, and
the input data for the second trained function includes an attenuation-corrected preliminary reconstructed image based on the respective corrected attenuation map.

20. The method of claim 16, wherein the attenuation map is only used for determining the first nuclear medical image data set and the input data for the second trained function includes a not attenuation-corrected preliminary reconstructed image.

* * * * *